United States Patent [19]
Saleh et al.

[11] Patent Number: 5,453,561
[45] Date of Patent: Sep. 26, 1995

[54] REACTIVE SEPARATION PROCESS

[75] Inventors: Ramzi Y. Saleh, Flemington; Michael Siskin, Morristown; Glen B. Brons, Phillipsburg, all of N.J.; Stephen N. Vaughn, Kingwood, Tex.; Richard H. Schlosberg, Bridgewater, N.J.

[73] Assignee: Exxon Research & Engineering Co., Florham Park, N.J.

[21] Appl. No.: 187,673

[22] Filed: Jan. 27, 1994

[51] Int. Cl.6 .................................................... C07C 7/00
[52] U.S. Cl. .................................................... 585/868
[58] Field of Search .............................................. 585/868

[56] References Cited

U.S. PATENT DOCUMENTS

| | | | |
|---|---|---|---|
| 2,519,061 | 8/1950 | Mason | 260/632 |
| 4,581,475 | 4/1986 | Neier et al. | 568/907 |
| 5,043,486 | 8/1991 | Siskin et al. | 568/907 |

OTHER PUBLICATIONS

Siskin, et al., Energy and Fuels vol. 4, p. 475 (1990).
Siskin, et al., Science vol. 254, pp. 231–237 (Oct. 11, 1991).

*Primary Examiner*—Anthony McFarlane
*Assistant Examiner*—Nhat D. Phan
*Attorney, Agent, or Firm*—Linda M. Scuorzo

[57] ABSTRACT

The invention concerns a method for reactive separation of mixtures containing hydrocarbons and oxygenated hydrocarbons, by contacting a mixture of hydrocarbons such as $C_2$ to $C_{26}$ hydrocarbons and mixtures thereof and oxygenated hydrocarbons, such as $C_2$ to $C_{40}$ oxygenated hydrocarbons and mixtures thereof to form a mixture of hydrocarbons and lower molecular weight oxygenated hydrocarbons and heating the mixture in water at temperature typically from about and pressure sufficient to cleave the oxygenated hydrocarbons to lower molecular weight products to form a liquid layer containing water soluble reaction products and an organic layer containing primarily hydrocarbons.

6 Claims, No Drawings

REACTIVE SEPARATION PROCESS

FIELD OF THE INVENTION

The present invention relates to a process for separating certain hydrocarbons from oxygenated hydrocarbons.

BACKGROUND OF THE INVENTION

A number of commercial processes produce higher value hydrocarbons, particularly high octane number branched alkenes, such as octenes in combination with oxygenated hydrocarbons such as sec-butyl ether, a $C_8$-derivative. For example, acid catalyzed hydration reactions of propylene and butenes (1-butene and cis and trans 2-butene) are used to manufacture isopropyl and sec-butyl alcohols, respectively. The sec-butyl alcohol is subsequently oxidized over a catalyst to produce 2-butanone (methyl ethyl ketone). Because of the nature of the reaction system, there are additional reactions which compete with the desired hydration reaction that form alcohols. The primary of these are olefin dimerization and the dehydration of two moles of alcohol to form ethers. In the case of the butene chemistry, dimerization of butenes ($C_4H_8$) will form a mixture of octenes ($C_8H_{16}$) in the presence of aqueous sulfuric acid under the reaction conditions employed in sec-butyl alcohol formation. In addition, acid catalyzed dehydration of two moles of sec-butyl alcohol also occurs in the process to form sec-butyl ether. The conversion of sec-butyl alcohol to sec-butyl ether produces $C_8$-ethers with boiling points which usually fall within the range of the boiling points of the product octenes. A process which would permit the selective separation and recovery of the hydrocarbons from mixed streams of hydrocarbons and oxygenated hydrocarbons would be a desirable upgrade option.

SUMMARY OF THE INVENTION

A method for reactive separation of mixtures containing hydrocarbons and oxygenated hydrocarbons, comprising contacting a mixture of hydrocarbons and oxygenated hydrocarbons that have sufficiently similar boiling points and heating the mixture in water at temperatures and pressures sufficient to cleave the oxygenated hydrocarbons to form lower molecular weight products which are either more volatile or that form an aqueous layer containing water soluble reaction products and, a second, organic layer containing primarily hydrocarbons. More particularly the hydrocarbons are typically selected from the group consisting of $C_2$ to $C_{26}$ hydrocarbons and mixtures thereof and oxygenated hydrocarbons are typically selected from the group consisting $C_2$ to $C_{40}$ oxygenated hydrocarbons and mixtures thereof. The reaction typically may be conducted at a temperature of from about 200° C. to about 450° C. and autogenous pressure. The process has utility in separations technologies.

DETAILED DESCRIPTION OF THE INVENTION

The present invention relates to a process for reactively separating oxygenated hydrocarbons from streams of mixed hydrocarbons and oxygenated hydrocarbons using water, wherein such oxygenated hydrocarbons and hydrocarbons have boiling points sufficiently similar to prohibit or prevent cost effective separation by boiling (e.g., by distillation or other conventional separation techniques known to those skilled in the art). While the process is most useful in the foregoing situation, it may also be used wherein the boiling points are more widely separated. Typically, e.g., oxygenated hydrocarbons may be selected from the group consisting of ethers, esters, acetals and mixtures thereof. Typically e.g., the hydrocarbons may be selected from the group consisting of paraffins, cycloparaffins, olefins, aromatics, and mixtures thereof. The reactive separation results in removal of oxygenated hydrocarbons as hydrolysis products from feedstreams or mixtures containing hydrocarbons and oxygenated hydrocarbons. Boiling points of the oxygenated hydrocarbons to be separated may be any boiling point, however, preferred are boiling points that fall within the range of the boiling points of at least one hydrocarbon in the reaction mixture from which it is to be separated.

The mixtures may take a variety of forms or be derived from a number of sources including direct hydration by-product streams containing those mixed components, oxo-bottoms streams, and other chemical process streams which today have low value. The process offers a simple method of reactively separating these components and recovering the hydrocarbons as an oxygenate free or oxygenate-reduced stream. The term "oxygenate" refers to any organic compound containing at least carbon, hydrogen and oxygen. As an added benefit, when the oxygenated hydrocarbon is, for example, an ether or ester, the process produces quantities of alcohols that can be sold as product in such potential applications as e.g., solvents, or feed for making plasticizers such as, e.g., phthalate esters. Olefins may also form which can be recovered and recycled to make more alcohols or other products.

As used herein the term "hydrocarbon" means compounds that contain only carbon and hydrogen. These hydrocarbons have uses known to those skilled in the art. For example, certain branched octenes, such as trimethylpentenes, have an octane number greater than 100 after hydrogenation and are used to increase the octane number of motor gasoline. Other $C_5$ to $C_{20}$ olefins have uses as feedstocks for oxonation/hydrogenation to the corresponding alcohols one carbon higher, for oxonation/oxidation to the corresponding acids one carbon higher, for Koch carbonylation in strong acid media to neo acids (2,2-2-trialkyl acetic acids), and for aromatic alkylation to make alkyl aromatics for a variety of end uses.

In the present invention, the starting mixture to be separated may be any feedstream or mixture containing hydrocarbons and oxygenated hydrocarbons. Typically, such starting mixtures may be obtained as by-products of such known processes such as the direct hydration of butenes to produce sec-butyl alcohol (and subsequently methyl ethyl ketone), or oxonation as practiced using cobalt technology as known in the art. In the oxonation process, an olefin is contacted with carbon monoxide/hydrogen at high pressure in the presence of a complex cobalt catalyst. The identified by-products from this process include, e.g., ethers, ether alcohols, esters, and acetals, which by-products find themselves as part of the so-called oxo-bottoms fraction which will be mixed with heavier olefins and paraffins in this stream.

The hydrocarbon starting materials for the process of the present invention are preferably $C_2$ to $C_{26}$ hydrocarbons, more preferably the hydrocarbon feedstream may contain $C_5$ to $C_{20}$ hydrocarbons; most preferred are $C_5$ to $C_{12}$ hydrocarbons. Paraffins, cycloparaffins, olefins, aromatics, alkyl aromatics, or mixtures thereof known to those skilled in the art as falling within the ranges of carbon atoms disclosed herein may suitably be used. Paraffins, olefins, and mixtures thereof are more preferred within the ranges disclosed herein; most preferred are olefins. In any event the hydrocarbon should be one that is not cleaved in water under the process conditions of the present invention.

The oxygenated hydrocarbons which may be used in the process of the present invention include $C_2$ to $C_{40}$ oxygenated hydrocarbons. Within the foregoing typical ranges include $C_5$ to $C_{20}$ and $C_{10}$ to $C_{40}$ (the latter particularly for oxo bottoms as starting materials for this process); $C_6$ to $C_{12}$ are more preferred and, most preferred are $C_6$ to $C_8$ oxygenated hydrocarbons. Oxygenated functionalities such as ethers, acetals, esters, and mixtures thereof falling within the ranges of carbon atoms disclosed herein are included within the term "oxygenated hydrocarbon". Oxygenated hydrocarbon starting materials also may be obtained as by-products of commercial processes and operations and are thus, generally, available as part of low value by-product streams. For example, a significant by-product stream in the conversion of 1-butene and 2-butenes to sec-butyl alcohol via direct hydration in sulfuric acid medium is a stream which contains largely $C_8$ olefins admixed with the $C_8$ oxygenated hydrocarbon, sec-butyl ether. Another stream containing significant amounts of reactive oxygenated hydrocarbons including ethers, alcohols, ether alcohols, esters, and acetals is the bottoms stream derived from oxonation of a variety of olefins, typically $C_5$ to $C_{12}$ branched olefin feeds.

Certain groups can interfere with the process of the present invention, e.g., by poisoning it and thereby decreasing the reaction rate. Typically this is seen when the feedstream or mixture contains reactive nitrogen containing compounds such as amines, amides and nitriles or other compounds that produce bases under hydrolysis conditions. Such competing reactions are not typically seen when the feedstream or starting mixture contains these reactive nitrogen species along with esters, because the esters undergo both acid and base catalyzed cleavage. One skilled in the art should, therefore, take into account that the nature of the feed stream can influence reaction rates in the process of the present invention.

The ratio of hydrocarbons to oxygenated hydrocarbons in the starting mixture will depend largely upon the source of the starting material (i.e. during the process which generated the particular mixture, feedstream, or by-products). Thus, a wide variation in content of the starting mixture or feedstock is possible, with the caveat that it should not contain compounds that would substantially poison or compete with the process of the present invention. It is not, therefore, desirable to have in the starting mixture components that would tend to render the hydrocarbons soluble in an aqueous phase or that would compete with the hydrolysis of the oxygenated hydrocarbons to a water soluble species. It is desirable that the number of carbon atoms in the hydrolysis or cleavage products of the oxygenated hydrocarbon starting materials be sufficiently different from than the number of carbon atoms in the starting hydrocarbons to render the oxygenated reaction products either more volatile or less volatile or sufficiently water soluble in an aqueous phase to be separable from hydrocarbons. Typically, e.g., the number of carbon atoms in the hydrolysis or cleavage products of the oxygenated hydrocarbons may be at least two less than the number of carbon atoms in the hydrocarbons. Generally, one would expect greater water solubility of oxygenated hydrocarbons containing $C_6$ or fewer carbon atoms than either $C_4$ or higher hydrocarbons or $C_7$ or higher oxygenated hydrocarbons.

Because of the similarities in solubility properties of certain materials even after cleavage or hydrolysis, the hydrocarbon layer may contain some higher molecular weight (i.e., longer carbon chain) oxygenates, typically alcohols. Thus, further or repeated separation may be necessary in some cases to remove those oxygenates from the hydrocarbon layer. Suitable separation procedures in such cases include distillation to remove the alcohol fraction.

In the process of the present invention, water is preferably present at reaction conditions (temperature and pressure) effective to maintain the water as a liquid. The ratio of water to the starting mixture of hydrocarbons and oxygenated hydrocarbons is desirably that which is effective to facilitate at least 50% cleavage or hydrolysis of the oxygenated hydrocarbon starting materials per pass. Typically a ratio of from 1:1 to 30:1 more typically about 2:1 to 10:1 weight of water to weight of oxygenated functionality is acceptable. However, to the extent that the amount of water can be reduced without affecting reaction yields, smaller amounts of water are more desirable.

The process may be conducted by introducing the water, the hydrocarbon, and oxygenated hydrocarbons into a reaction vessel and heating the mixture under autogeneous pressure and preferably in an inert atmosphere, such as argon or nitrogen, as an aid in excluding oxygen from the system, and at a temperature within the range of from about 200° to about 450° C. for a period of time sufficient to convert the oxygenated hydrocarbon into other products of lower molecular weight. The process may be conducted toward the lower end of any disclosed range, with the recognition that the required times for cleavage may increase accordingly. Normally, the processes would be conducted at a temperature not higher than the critical temperature of water which is about 374.4° C., but supercritical temperatures above temperature and up to about 450° C. may be used. The temperature of the water in the final reaction mixture of hydrocarbon and oxygenated hydrocarbons also may be adjusted to increase solubility for separability of the resulting oxygenated hydrocarbons.

The term "autogeneous pressure of the system" refers to the combined vapor pressure exerted by the mixed components present in the aqueous system heated at a particular process temperature. The autogeneous pressure of water alone in such a system ranges from about 500 psia (3.45 MPa) to 3200 psia (22.06 MPa) over a temperature range of from about 250° C. up to about 374.4° C., the critical temperature of water. Obviously, the autogeneous pressure of a system containing both water, oxygenated hydrocarbons and hydrocarbons would be higher over this temperature range as a function of the content and the partial pressure exerted by the oxygenated hydrocarbon and hydrocarbon components.

In some cases it may be desirable to also add small quantities of an acid to the reaction mixture, the presence of the acid can enhance the conversion rate. Thus, in a second aspect of the invention the reaction mixture may contain a mixture of water, oxygenated hydrocarbons, hydrocarbons and may further include less than 3% by weight of acid component sufficient to develop a weakly acidic aqueous mixture having a pH within the range of from about 3.5 up to about less than 7 at room temperature. The addition of stronger acids such as sulfuric, hydrochloric or phosphoric to the aqueous reaction media at levels of less than about 0.5% by weight gives rise to higher conversion rates but tends to disfavor selectivity towards the yield of alcohols and favor selectivity towards the production of olefins or other by-products. In partial contrast, the addition of weaker acids such as acetic acid or finely divided aluminosilicate materials to the aqueous reaction medium at levels of less than about 3% by weight also tends to give rise to higher ether conversion rates, but greater selectivity towards the yield of alcohols. Thus, the process may be further modified by the inclusion of acidic materials in the reaction media to enhance ether conversion and influence selectivity toward the production of alcohols on one hand or other by-products on the other, depending on the identity of, strength of, and concentration of the acid.

The process may be used to reduce the molecular weight of the oxygenated hydrocarbons as compared to the molecular weight of the oxygenated hydrocarbons in the starting mixture by producing lower molecular weight hydrocarbons and/or oxygenated hydrocarbons as reaction products from the starting materials. Typically these lower molecular oxygenates can further enhance the solubility of the unconverted or remaining oxygenated hydrocarbons in the aqueous layer which would further enhance the separation.

The invention disclosed herein may suitably comprise, consist, or consist essentially of the elements disclosed herein.

EXAMPLE 1

All materials (except those indicated) were obtained from commercial sources and used without further purification. The reaction was carried out in liquid water at 315° C. for the time period indicated, in a T-316 stainless steel reactor bomb having a capacity of 11 cc. The reactor was sealed under argon and the reaction mixture was heated in a sand bath for 30 minutes unless a different time is specified. The reactor was then cooled to room temperature, and extracted with diethyl ether. A 5 w/w mixture of the water to sec-butyl ether was used. The sec-butyl ether ("SBE-Ex") was Exxon grade, i.e., 62.8% sec-butyl ether, with the remainder essentially a mixture of branched octenes. The process produced a 59% conversion of the initial sec-butyl ether component to butenes and sec-butyl alcohol, the octenes remained unreacted.

EXAMPLE 2

A heavy fraction by-product of the Oxo process containing a mixture of dimers, trimers, and tetramers (i.e., ethers, esters, acetals) in admixture essentially with olefins is heated in a 5-fold excess of $H_2O$ at 350° C. for 2 hours. The reaction hydrolyzes the ethers to oxo-alcohols acetals, and hemiacetals to alcohols and aldehydes, and esters to acids and alcohols. The unreacted olefins form a second, separate layer with some hydrocarbon-soluble alcohols. The layer which contains the cleaved or hydrolyzed oxygenated products, which are more water soluble is separated from the hydrocarbon layer.

What is claimed is:

1. A method for reactively separating mixtures containing hydrocarbons and oxygenated hydrocarbons, consisting essentially of the steps of:

heating a starting mixture of hydrocarbons selected from the group consisting of $C_2$ to $C_{26}$ hydrocarbons and mixtures thereof and oxygenated hydrocarbons selected from the group consisting of $C_2$ to $C_{40}$ oxygenated hydrocarbons and mixtures thereof in water at temperature and pressure sufficient to cleave the oxygenated hydrocarbons to lower molecular weight hydrocarbon and oxygenated hydrocarbon products; and forming an aqueous layer containing lower molecular weight oxygenated hydrocarbon reaction products having solubility in water and an organic layer containing primarily hydrocarbons.

2. A method for reactively separating mixtures containing hydrocarbons and oxygenated hydrocarbons, consisting essentially of the steps of:

heating a starting mixture of hydrocarbons selected from the group consisting of $C_2$ to $C_{26}$ hydrocarbons and mixtures thereof and oxygenated hydrocarbons selected from the group consisting of $C_2$ to $C_{40}$ oxygenated hydrocarbons and mixtures thereof in water at a temperature and pressure sufficient to cleave oxygenated hydrocarbons to lower molecular weight hydrocarbon and oxygenated hydrocarbon reaction products;

forming an aqueous layer containing lower molecular weight oxygenated hydrocarbon reaction products having solubility in water and an organic layer containing primarily hydrocarbons; and separating the reaction products having solubility in water to recover the lower molecular weight oxygenated hydrocarbon reaction product.

3. The method of claim 1 wherein the oxygenated hydrocarbons are selected from the group consisting of ethers, esters, acetals, and mixtures thereof and the hydrocarbons are selected from the group consisting of paraffins, olefins, aromatics and mixtures thereof.

4. The method of claim 1 wherein the hydrocarbons are selected from the group consisting of $C_6$ to $C_{12}$ olefins and mixtures thereof and wherein the oxygenated hydrocarbons are selected from the group consisting of $C_6$ to $C_{12}$ ethers and mixture thereof.

5. The method of claim 1 wherein the hydrocarbon is a mixture of $C_8$ olefins and the oxygenated hydrocarbon is sec-butyl-ether.

6. The method of claim 1 wherein the hydrocarbon is a mixture of olefins and the oxygenated hydrocarbons are selected from the group selected consisting of $C_{10}$ to $C_{40}$ oxygenated hydrocarbons.

* * * * *